(12) United States Patent
Hegland et al.

(10) Patent No.: US 7,668,601 B2
(45) Date of Patent: Feb. 23, 2010

(54) IMPLANTABLE MEDICAL LEAD WITH MULTIPLE ELECTRODE CONFIGURATIONS

(75) Inventors: Michael T. Hegland, Mounds View, MN (US); James M. Olsen, Plymouth, MN (US); Gabriela C. Miyazawa, New Brighton, MN (US); Richard T. Stone, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 466 days.

(21) Appl. No.: 11/740,643

(22) Filed: Apr. 26, 2007

(65) Prior Publication Data

US 2008/0269854 A1    Oct. 30, 2008

(51) Int. Cl.
*A61N 1/04* (2006.01)
(52) U.S. Cl. .................................... 607/116
(58) Field of Classification Search .................. 607/116
See application file for complete search history.

(56) References Cited

U.S. PATENT DOCUMENTS

| | | |
|---|---|---|
| 4,961,434 A | 10/1990 | Stypulkowski |
| 5,000,194 A | 3/1991 | van den Honert et al. |
| 5,423,877 A | 6/1995 | Mackey |
| 5,522,874 A | 6/1996 | Gates |
| 5,649,970 A | 7/1997 | Loeb et al. |
| 5,800,465 A | 9/1998 | Thompson et al. |
| 5,843,148 A | 12/1998 | Gijsbers et al. |
| 6,038,480 A | 3/2000 | Hrdlicka et al. |

(Continued)

FOREIGN PATENT DOCUMENTS

EP          0 832 667 A2    4/1998

(Continued)

OTHER PUBLICATIONS

"Notification of Transmittal of the International Search Report and the Written Opinion," dated Feb. 4, 2008 for corresponding PCT Application No. PCT/US2007/010202 (11 pgs.).

(Continued)

*Primary Examiner*—Carl H Layno
*Assistant Examiner*—Yun Haeng Lee
(74) *Attorney, Agent, or Firm*—Shumaker & Sieffert, P.A.

(57) ABSTRACT

Medical leads having at least one segmented row of electrodes, as well as at least one ring electrode that extends substantially completely around the periphery of the lead, are described. The electrodes in a segmented row extend around only a portion of the periphery of the lead, rather than substantially around the entire periphery. The electrodes in a segmented row may be distributed at respective locations around the periphery of the lead and separated by insulating material. The ring electrodes and segmented rows are located at respective axial positions. For example, in some embodiments, a plurality of segmented rows, such as two rows having three electrodes each, are located between two ring electrodes. Such a lead may, for example, provide a variety of stimulation modalities because of localized stimulation capabilities.

41 Claims, 4 Drawing Sheets

U.S. PATENT DOCUMENTS

| | | |
|---|---|---|
| 6,473,653 B1 | 10/2002 | Schallhorn et al. |
| 6,493,590 B1 | 12/2002 | Wessman et al. |
| 6,510,347 B2 | 1/2003 | Borkan |
| 6,757,970 B1 | 7/2004 | Kuzma et al. |
| 2002/0183817 A1 | 12/2002 | Van Venrooij et al. |
| 2003/0083724 A1 | 5/2003 | Jog et al. |
| 2004/0098074 A1 | 5/2004 | Erickson et al. |
| 2006/0168805 A1 | 8/2006 | Hegland et al. |
| 2006/0173262 A1 | 8/2006 | Hegland et al. |

FOREIGN PATENT DOCUMENTS

| | | |
|---|---|---|
| WO | WO 02/068042 | 9/2002 |
| WO | WO 2006/013345 | 12/2006 |

OTHER PUBLICATIONS

"Notification of Transmittal of the International Preliminary Report on Patentability," dated Jun. 18, 2009 for corresponding PCT Application No. PCT/US2007/010202 (8 pgs.).

"Reply to Written Opinion" dated Jun. 18, 2008 for corresponding PCT Application No. PCT/US2007/010202 (9 pgs.).

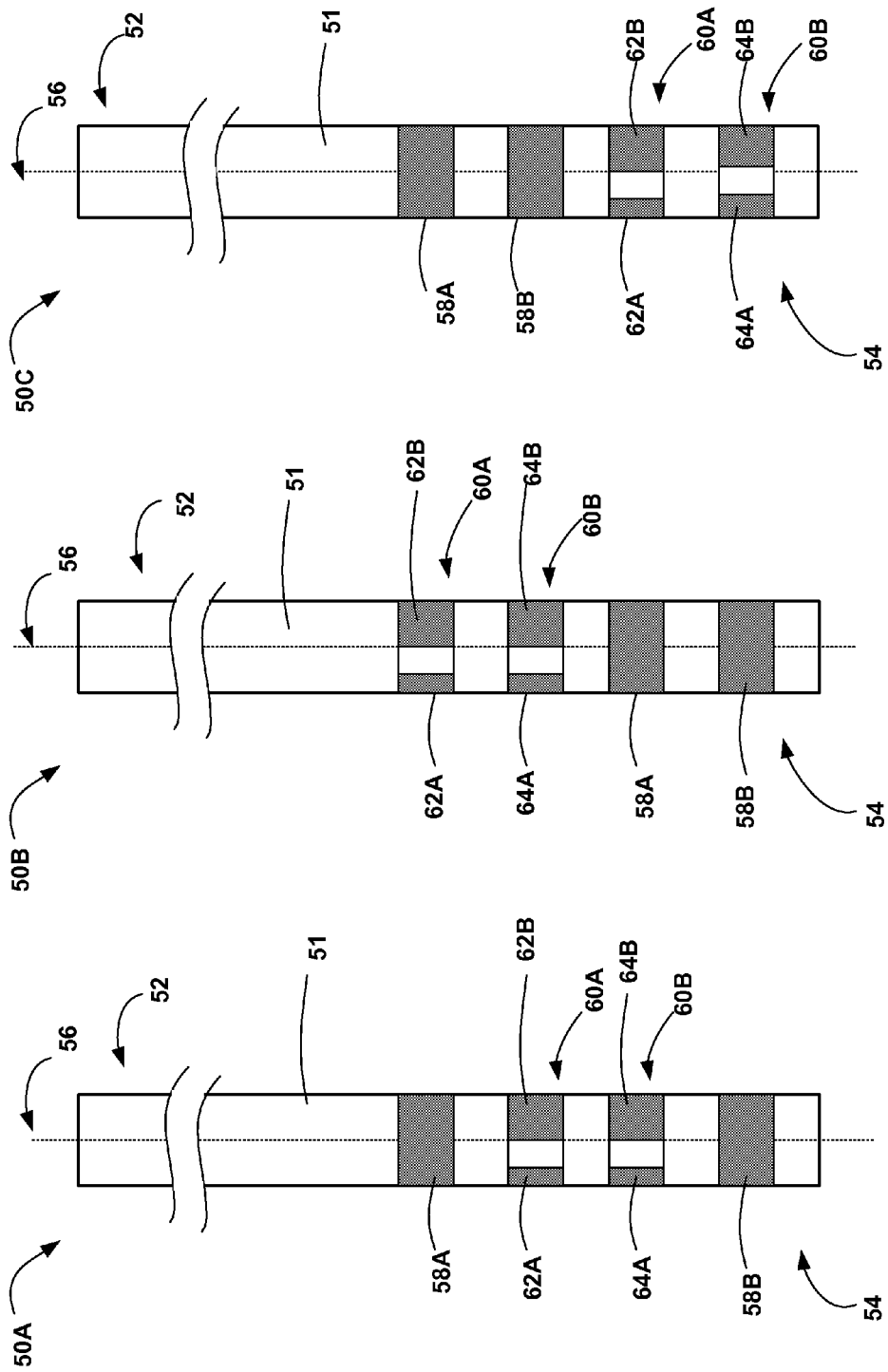

IMPLANTABLE MEDICAL LEAD WITH MULTIPLE ELECTRODE CONFIGURATIONS

TECHNICAL FIELD

The invention relates to medical devices, more particularly to implantable medical leads.

BACKGROUND

The medical device industry produces a wide variety of electronic and mechanical devices for treating patient medical conditions, such as pacemakers, defibrillators, neurostimulators, and therapeutic substance delivery pumps. Medical devices may be configured to be surgically implanted or connected externally to a patient receiving treatment. Clinicians may use medical devices alone or in combination with therapeutic substance therapies and surgery to treat patient medical conditions. For some medical conditions, implantable medical devices provide the best and sometimes the only therapy to restore an individual to a more healthy condition and fuller life.

An implantable neurological stimulation system may be used to treat conditions such as pain, movement disorders, epilepsy, depression, pelvic floor disorders, gastroparesis, or a wide variety of other medical conditions. Such a neurostimulation system typically includes an implantable neurostimulator and a medical electrical stimulation lead. A lead extension may also be used. Medical electrical stimulation leads have one or more electrodes, which may be implanted within or proximate to a specific location in a patient to deliver stimulation to structures or tissues to a target location in the patient. Some therapies involve electrical stimulation of the brain, spinal cord, or pelvic floor. Still other therapies involve electrical stimulation of other sites in the patient.

As one example, deep brain stimulation (DBS) involves delivery of electrical stimulation to nerve structures in specific areas of the brain to either excite or inhibit cell activity. A stimulation lead is typically implanted at a desired location within the brain with relative precision using magnetic resonance (MR) imaging techniques and stereotactic guidance. DBS can be effective in the management of, for example chronic pain, movement disorders such as Parkinson's disease and essential tremor, epilepsy, and psychiatric disorders such as depression and obsessive-compulsive disorder.

Precise placement of the stimulation lead within the brain is important. In some applications, it is desirable to position the stimulation lead to deliver stimulation to a very small target site without stimulating adjacent brain tissue. If stimulation is not delivered with precision to a desired target site, adjoining areas may also be stimulated, which may lead to undesirable side effects.

Segmented rows of electrodes, in which each of the electrodes does not extend around the full periphery, e.g., circumference, of the lead body, may be desired for targeted stimulation or for efficient use of energy. With respect to targeted stimulation, electrodes in segmented rows may, for example, generate stimulation fields that are skewed in a particular radial direction from the lead, as opposed to the fields produced by ring electrodes, which are substantially equal in all radial directions when stimulating within homogeneous tissue. The ability to direct the stimulation field in this manner may permit particular stimulation targets to be activated, while avoiding other areas. This ability may be advantageous in the case of DBS, as well as other types of stimulation in which such precision is desired.

SUMMARY

In general, the invention is directed to a medical lead having at least one segmented row of electrodes, as well as one or more ring electrodes that extend substantially completely around the periphery of the lead. Each of the electrodes within a segmented row extends around only a portion of the periphery of the lead, rather than substantially around the entire periphery. The electrodes of a segmented row may be distributed at respective locations around the periphery of the lead and separated by insulating material.

The ring electrodes and segmented rows of electrodes are located at respective axial positions. For example, in some embodiments, a plurality of segmented rows of electrodes, such as two segmented rows having three electrodes each, are located between two ring electrodes. However, the medical lead may include any number of ring electrodes and segmented rows, and each segmented row of electrodes may include any number of electrodes, which may be the same or different across a plurality of segmented rows.

In one embodiment, the invention is directed to a medical lead comprising an elongated lead body that includes a proximal portion configured for coupling the medical lead to a stimulation controller and a distal portion, wherein the lead body defines a longitudinal axis. The medical lead further comprises a first ring electrode and a second ring electrode respectively located at first and second axial positions on the distal end of the lead body, and at least one segmented row of electrodes at a third axial position on the distal end of the lead body.

In another embodiment, the invention is directed to a medical lead comprising an elongated lead body that includes a proximal portion configured for coupling the medical lead to a stimulation controller and a distal portion, wherein the lead body defines a longitudinal axis. The medical lead further comprises a first ring electrode and a second ring electrode respectively located at first and second axial positions on the distal end of the lead body. The medical lead further comprises a first segmented row of electrodes at a third axial position of the distal end of the lead body, and a second segmented row of electrodes at a fourth axial position on the distal end of the lead body.

In another embodiment, the invention is directed to a system comprising any of the medical leads described herein, and a stimulation controller that delivers electrical stimulation via a selected combination of the plurality of electrodes of the medical lead.

Embodiments of the invention may provide advantages. For example, a medical lead with both ring electrodes and segmented rows of electrodes may provide flexibility with respect to stimulation fields, including targeted stimulation utilizing the smaller electrodes in the segmented rows, or stimulation utilizing both ring electrodes and electrodes within segmented rows. In some embodiments, the segmented rows may be positioned between the ring electrodes, e.g., near the middle of the electrode region on the distal portion of the lead. In such embodiments, a clinician may implant the lead with the intent to place the segmented rows proximate to a stimulation target. Even if the placement is not precise or the lead moves, the ring electrodes and/or the electrodes on the segmented rows may be able to provide efficacious stimulation to the target.

Furthermore, in some cases, the physiologically appropriate site for delivery of stimulation may be different than the anatomical target chosen by the clinician. In such cases, stimulation may be less efficacious than desired, even if the lead placement is accurate. However, in such cases, the ring electrodes and/or the electrodes on the segmented rows of leads according to the invention may be able to provide efficacious stimulation to the physiological appropriate site.

Additionally, the number of electrodes on a lead may be selected to conform to a number of electrodes supported by existing stimulation devices. For example, a number of existing stimulation devices support up to eight electrodes per lead. A medical lead including only four segmented rows with two electrodes each and no ring electrodes may not provide the desired degree of directability of the stimulation. A medical lead with only two segmented rows of four electrodes each may require relatively high precision on the part of the clinician to implant the segmented rows proximate to a target, or may be unable to provide stimulation with the desired efficacy in cases in which the physiological appropriate site for stimulation is different than the anatomical target. A medical lead with segmented rows of four electrodes may also result in relatively small electrode sizes, with higher charge densities at equivalent amplitudes than larger electrodes in rows with fewer electrodes, such as lead with two segmented rows of three electrodes, and two ring electrodes.

A medical lead with two segmented rows of three electrodes may mitigate side effects. Further, providing a ring electrode on the lead may be beneficial if the implantation of the lead was not adequately precise, or the physiologically appropriate site for stimulation is different than the anatomical target selected by the clinician. The ring electrode may act as a fall-back for stimulation if the rows of segmented electrodes were not positioned, for whatever reason, proximate to the physiologically appropriate tissue for stimulation. Also, the presence of the ring electrode at the most distal position on the lead may reduce the amount of heating on the lead during magnetic resonance imaging relative to leads including only segmented rows of smaller electrodes.

The details of one or more embodiments of the invention are set forth in the accompanying drawings and the description below. Other features, objects, and advantages of the invention will be apparent from the description and drawings, and from the claims.

BRIEF DESCRIPTION OF DRAWINGS

FIGS. 4A-4C are side views of other example medical leads with different electrode configurations at different axial positions.

DETAILED DESCRIPTION

Figure 1:
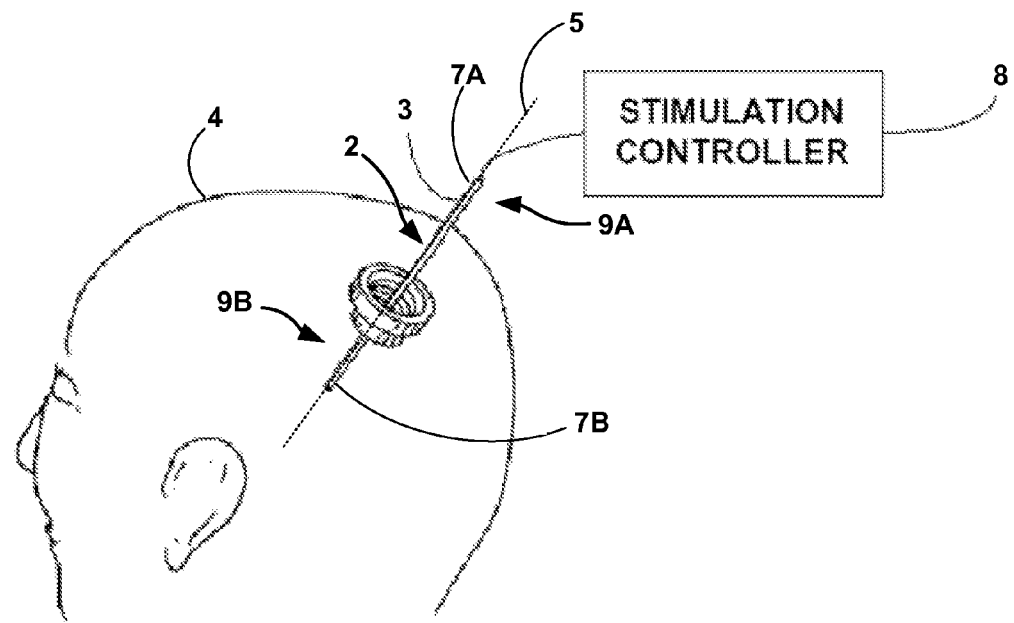
FIG. 1 illustrates an example environment in which a medical lead that includes different electrode configurations at different axial positions may be employed.

FIG. 1 illustrates one example environment in which medical lead 2, which includes different electrode configurations at different axial positions, may be employed. More particularly, FIG. 1 illustrates insertion of medical lead 2 into the brain of patient 4 via a burr hole through the cranium of patient 4. Lead 2 includes an elongated lead body 3 that includes a proximal portion 9A and a distal portion 9B and defines a longitudinal axis 5. Proximal end 7A on proximal portion 9A of lead 2 is electrically coupled to a stimulation controller 8. Proximal end 9A may be, for example, coupled directly to the stimulation controller, or coupled to a lead extension that is in turn coupled to the stimulation controller.

Stimulation controller 8 may supply stimulation to various electrodes carried by lead 2. In addition, stimulation controller 8 may receive signals from one or more of the electrodes of lead 2 to sense and record brain activity proximate to a desired target site. Stimulation controller 8 may be an implantable medical device (IMD) or an external medical device.

With distal portion 9B of lead 2, including a distal end 7B, positioned in the brain of patient 4, stimulation controller 8 may deliver deep brain stimulation (DBS) to target nerve structures in specific areas of the brain of patient 4 to treat, for example, chronic pain, movement disorders (e.g., Parkinson's disease), epilepsy, psychiatric disorders, or other disorders. In some embodiments, stimulation controller 8 may deliver stimulation via the one or more of the electrodes of lead 2 in response to electrical signals detected via one or more of the electrodes. For example, stimulation controller 8 may deliver stimulation to terminate a seizure based on electrical signals detected via one or more of the electrodes. In some embodiments, stimulation controller 8 may deliver stimulation to specific and relatively small structures within the brain via the electrodes of lead 2, such as the SubThalamic Nucleus (STN) or Globus Pallidus internal (Gpi).

However, the invention is not limited to DBS. For example, lead 2 may be implanted to deliver stimulation to the spinal cord, pelvic floor, gastrointestinal tract, or any of the peripheral nerves to treat pain, sexual dysfunction, incontinence, gastroparesis, respiratory disorders, or any other disorders. Additionally, although a single lead 2 is illustrated in FIG. 1, two or more leads may be implanted, one or more of which may include different electrode configurations at different axial positions as described herein.

Figure 2:
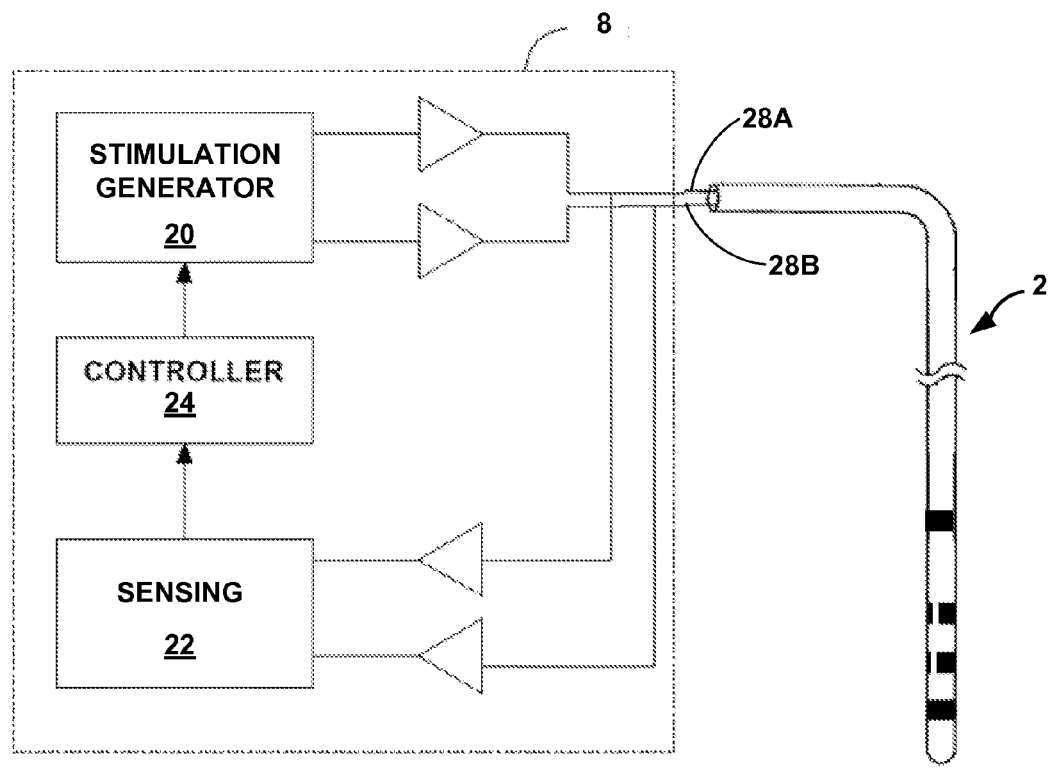
FIG. 2 is a functional block diagram illustrating an example medical lead with different electrode configurations at different axial positions coupled to a stimulation controller.

FIG. 2 is a functional block diagram illustrating stimulation controller 8 in greater detail. As shown in FIG. 2, stimulation controller 8 may include stimulation generator 20, sensing circuitry 22, and controller 24. In operation, sensing circuitry 22 conditions signals obtained from one or more of the electrodes carried by lead 2 for processing and analysis by controller 24. Sensing circuitry 22 may include various filters, analog to digital converters, and/or other signal conditioning circuitry. The recorded signals may be used for analysis, triggering of stimulation generator 20, or both. For example, controller 24 may be responsive to brain activity signals sensed by sensing circuitry 22 via lead 2, and thereby activate stimulation generator 20 to deliver electrical stimuli to one or more of the electrodes carried by lead 2. As discussed above, however, according to some embodiments, stimulation controller 8 need not include sensing circuitry 22, or deliver responsive stimulation.

In the example of FIG. 2, two conductors 28A and 28B (collectively "conductors 28") are shown. However, the number of conductors 28, and associated sensing and stimulation output channels, may vary. For example, some embodiments may include four, eight, or more conductors 28 per lead. In general, the number of conductors will correspond to the number of electrodes on lead 2.

Stimulation controller 8 may be, for example, a stimulator from the Restore product line available from Medtronic, Inc. of Minneapolis, Minn., or a modification of such a device. Controller 24 may comprises a microprocessor, application specific integrated circuit (ASIC), field programmable gate array (FPGA), and/or other digital or control and timing circuitry. In addition, controller 24 may control switching circuitry of stimulation generator 20 to switch the output of stimulation current generator 20 between different conductors 28 that carry stimulation current to the electrodes of lead 2. In this manner, controller 24 may facilitate delivery of stimulation via selected combinations of the electrodes carried by lead 2.

The stimulation may be bipolar between two or more of the electrodes on lead 2. However, in some embodiments, an electrode on the housing of stimulation controller 8, or the housing itself, may be used as an electrode for use in a monopolar stimulation configuration. Further, in some embodiments, a proximal electrode on lead 2 is located away from the other electrodes and configured as an anode to facilitate pseudo-monopolar stimulation, as will be described in greater detail below.

Figure 3:
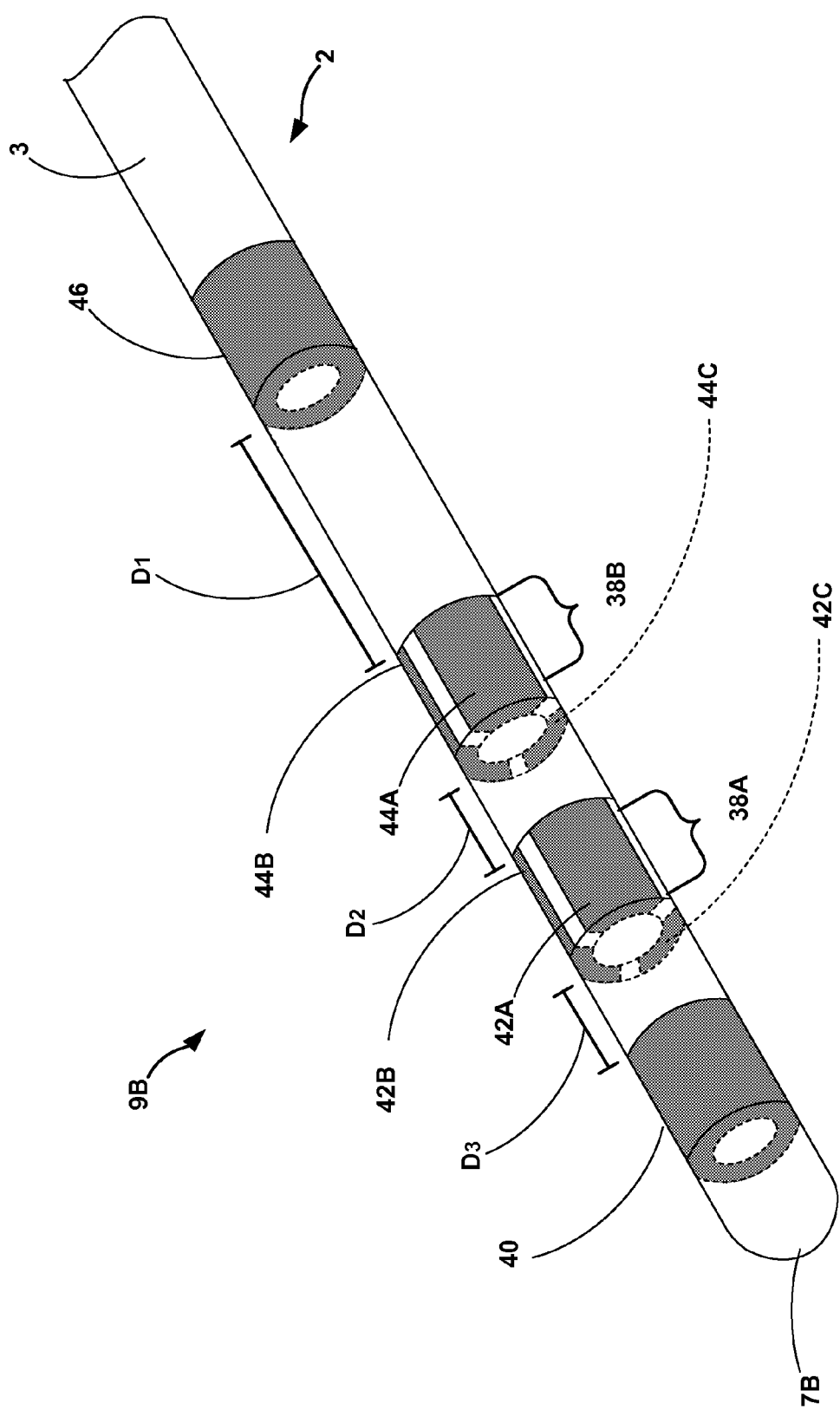
FIG. 3 is a perspective view of the distal portion of an example medical lead with different electrode configurations at different axial positions.

FIG. 3 is a perspective view of distal portion 9B, i.e., the portion implanted proximate to a target site for delivery of stimulation and/or sensing, of medical lead 2 including distal end 7B. As shown in FIG. 3, lead body 3 of lead 2 may be tubular in form and may have a substantially circular cross-section. However, the invention is not so limited. Lead body 3 of lead 2 may have any cross-sectional shape, such as rectangular, triangular, or other polygonal cross-sectional shapes, which may vary over the length of lead 2. An outer surface of lead body 3 may be formed from a biocompatible material such as, for example, polyurethane or silicone.

One or more ring electrodes 40 and 46 may be distributed at respective axial positions along the length of lead 2 (measured from proximal end 7A to distal end 7B as shown in FIG. 1). Ring electrodes 40 and 46 extend substantially around the entire periphery, e.g., circumference, of lead body 3. In embodiments in which lead body 3 of lead 2 has a substantially circular cross-section, such as the embodiment illustrated in FIG. 3, ring electrodes 40 and 46 may be circular ring electrodes. However, the use of the term "ring" herein is not limited to circular shaped electrodes that encircle the periphery of the lead body. Instead, a "ring electrode" is an electrode of any shape that extends substantially around the entire periphery of the lead body.

Distal portion 9B of lead 2 also includes segmented rows 38A and 38B (collectively rows 38) at respective axial positions on lead body 3. Rows 38A and 38B include electrodes 42A-42C (collectively electrodes 42) and 44A-44C (collectively electrodes 44), respectively. Electrodes 42C and 44C are located on the circumferential portion of lead 2 not visible in FIG. 3. The approximate locations of electrodes 42C and 44C are outlined with dotted lines.

Electrodes 42 and 44 do not extend substantially around the entire periphery of the lead body 3. Each of electrodes 42 and 44 in segmented rows 38 may, for example, extend through arcs of 60, 80, 90, or as many as 119 degrees, although the invention is not limited to these dimensions. Electrodes 42 and 44 in segmented rows 38 may be, but need not be, evenly spaced around the periphery of lead 2. Each of electrodes 40-46 can be made from an electrically conductive, biocompatible material, such as platinum iridium. In addition, one or more of electrodes 40-46 may function as sensing electrodes that monitor internal physiological signals of patient 4 (FIG. 1).

In the illustrated embodiment, lead 2 includes two ring electrodes 40 and 46 that extend substantially around the entire periphery of lead 4, and two segmented rows 138 of electrodes 42 and 44. In the illustrated embodiment, ring electrodes 40 and 46 occupy the most proximal and distal axial positions (along the length of lead 2 measured from proximal end 2A to distal end 2B), while rows 138, each with three electrodes 42 and 44, are located in between. This configuration may be referred to as a 1-3-3-1 electrode configuration, where each axial position is represented by a number that indicates the number of electrodes at that respective axial position, and the numbers representing each position are ordered from the most distal to the most proximal axial position.

In some embodiments, the distances between each of the axial positions (e.g., the positions of segmented rows 38 and ring electrodes 40 and 46) may be approximately equal. However, the invention is not limited in this manner. FIG. 3 illustrates one embodiment in which the distance between ring electrode 46 at the most proximally located axial position and the adjacent axial position, e.g., row 38B, is greater than the distances between the other adjacent axial positions. e.g., the distance between rows 38A and 38B, and the distance between row 38A and ring electrode 40.

By placing ring electrode 46, which is located at the most proximal axial position, at a substantial distance from the rest of the electrodes (e.g., electrodes 40, 42, and 44), ring electrode 46 may be used to provide pseudo-monopolar stimulation when activated as an anode. Because of the distance between the proximal anode and the other electrodes on lead 2, stimulation using ring electrode two as an anode may approximate monopolar stimulation using the housing of stimulation controller 8 (FIG. 1), or an electrode located thereon, as an anode.

In order to effectively mimic monopolar stimulation, ring electrode 46 may be axially displaced from the other electrodes (e.g., electrodes 40, 42, and 44) on lead 2. For example, distance $D_1$ between ring electrode 46 at the most proximal axial position and row 38B at the adjacent axial position may be greater than approximately 3 millimeters, greater than approximately 5 millimeters, or greater than approximately 10 millimeters. In some embodiments, distance D1 may be at least approximately two times greater than one or more of distances $D_2$ and $D_3$ between the other adjacent axial positions. In other embodiments, distance D1 may be at least approximately three times greater than one or more of distances $D_2$ and $D_3$ between the other adjacent axial positions. In some embodiments, electrodes 40, 42, and 44 may be implanted proximate to a target stimulation site (e.g., within the brain of patient 4 of FIG. 1), and electrode 46 may be located at a distance from the target stimulation site (e.g., outside of the skull within the scalp of patient 4).

Further, in some embodiments, although not illustrated in FIG. 3, lead 2 may be coupled to stimulation controller 8 by one or more lead extensions. In some embodiments, electrode 46 may be located on a lead extension that couples lead 2 to stimulation controller 8. In other embodiments, electrode 46 may be located on a connector between lead 2 and a lead extension that couples lead 2 to stimulation controller 8.

Although ring electrode 46 is located at the most proximal axial position in the embodiment illustrated in FIG. 3, in some embodiments, a segmented row of electrodes may be positioned at the most proximal axial position. In these embodiments, one or more of the electrodes within the segmented row at the most proximal axial position may be activated as an anode to provide pseudo-monopolar stimulation that mimics using the casing of stimulation controller 8 (FIG. 1) as an anode. As described in further detail below, increasing the size of the electrode(s) located at the most proximally located axial position may more accurately mimic a monopolar stimulation configuration that uses the casing of stimulation controller 8 (FIG. 1) as an anode.

FIGS. 4A-4C are side views of example medical leads 50A-50C (collectively leads 50) with different electrode configurations at different axial positions. As illustrated in FIGS. 4A-4C, leads 50 each include an elongated lead body 51 that includes a proximal portion 52 and a distal portion 54. Proximal portions 52 may include connectors for coupling leads 50 to stimulation controller 8. Distal portions 54 may be implanted proximate to target tissue site for stimulation, such as a target structure within the brain of patient 4 (FIG. 1). The elongated lead body 51 of each of leads 50 defines a longitudinal axis 56.

Each of leads 50 includes ring electrodes 58A and 58B (collectively electrodes 58) that extend substantially completely around the periphery of lead body 51, as well as segmented rows 60A and 60B (collectively rows 60) that include electrodes 62A-62B (collectively electrodes 62) and 64A-64B (collectively electrodes 64), respectively. Although only two electrodes in each row are visible, each of rows 60 may include any number of electrodes, and each of rows 60 may include the same or different numbers of electrodes. Further, although the electrodes 62 and 64 of rows 60 are illustrated as being substantially aligned on a common plane perpendicular to longitudinal axis 56, i.e., coplanar, the electrodes of a segmented row that is located at a particular axial position (e.g., electrodes 62 of row 60A) may be arranged in a non-coplanar fashion, e.g., diagonally, with respect to the longitudinal axis. Also, electrodes 62 and 64 in different rows may, but need not be oriented substantially parallel, e.g., in columns, in the direction of longitudinal axis 51.

Leads 50 illustrate a few examples of possible arrangements of two ring electrodes 58 and two segmented rows 60 of electrodes 62 and 64 with respect to axial position (i.e., position along longitudinal axis 56). In particular, lead 50A includes two segmented rows 60 between two ring electrodes 58 as was also illustrated with respect to lead 2 in FIG. 3. Lead 50B includes ring electrodes 58 at the more distal axial positions, while lead 50C illustrates ring electrodes 58 at the more proximal axial positions. Thus, if each of segmented rows 60 included three electrodes, leads 50A-50C respectively include 1-3-3-1, 1-1-3-3, and 3-3-1-1 electrode configurations (where each axial position is represented by a number that indicates the number of electrodes at that respective axial position and the numbers representing each position are ordered from the most distal to most proximal axial position).

The invention is not limited to the illustrated configurations. For example, some embodiments include configurations in which ring electrodes 58 and segmented rows 60 alternate, e.g., 1-3-1-3 or 3-1-3-1. Further, the invention is not limited to the illustrated numbers of ring electrodes 58, segmented rows 60, or electrodes per each one of segmented rows 60. Various embodiments may include any one or more ring electrodes 58 that extend substantially completely around the periphery of lead body 51, and any one or more segmented rows 60 of electrodes.

Figure 5A:
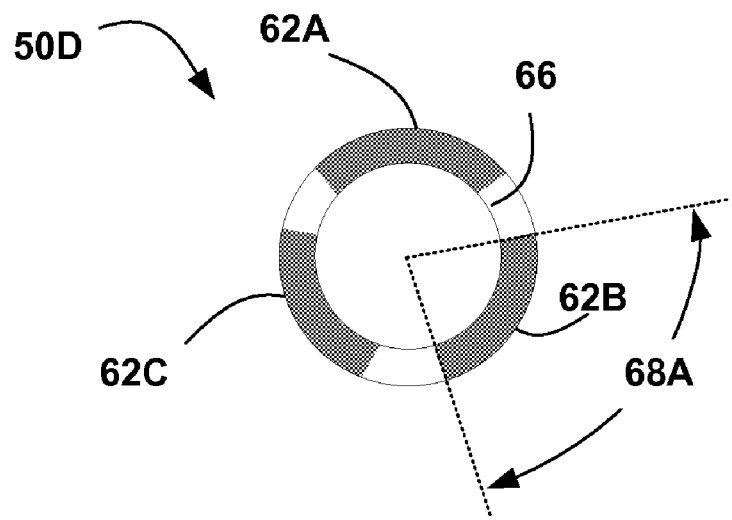
FIGS. 5A and 5B are transverse cross-sectional views of example medical leads with different electrode configurations at different axial positions.
Figure 5B:
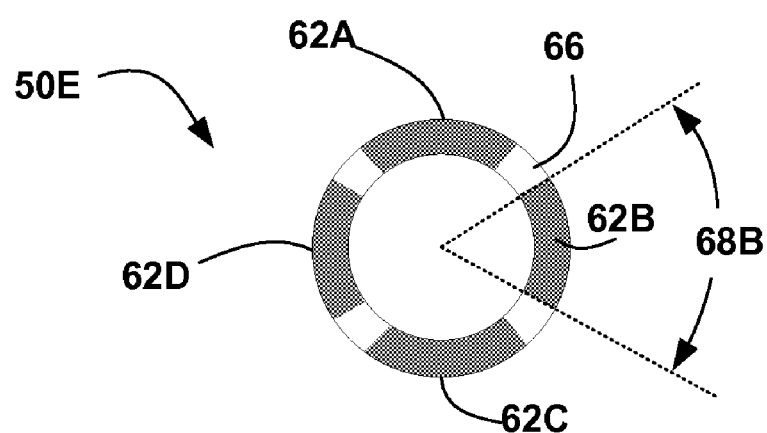

FIGS. 5A and 5B are cross-sectional views of example medical leads 50D and 50E with different electrode configurations at different axial positions. More particularly, FIGS. 5A and 5B respectively illustrate cross-sections taken through a segmented row of electrodes 63A-63C (collectively electrodes 63) and 65A-65D (collectively electrodes 65). As illustrated by FIGS. 5A and 5B, a segmented row may include any number of electrodes, including three (63A-63C) or four (65A-65D) electrodes as illustrated by FIGS. 5A and 5B, respectively. Although the invention is not so limited, electrodes 63 and 65 are distributed evenly about the periphery of lead body 51, and separated by insulating material 66. Further, each of electrodes 63 and 65 within a segmented row defines an arc 68A and 68B. Arcs 68 may extend anywhere from about 1 degree of arc to about 179 degrees of arc. As examples, arcs 68 may be greater than approximately 40 degrees, greater then approximately 60 degrees, or greater than approximately 80 degrees, or approximately 90 degrees. The arcs defined by each electrode of a segmented row may, but need not be the same. Further, as between different rows, the arcs defined by the electrodes may, but need not be the same.

A lead with at least one ring electrode and at least one segmented row of electrodes as depicted in FIGS. 3-4C, may provide localized stimulation therapy and decreased heating during MR imaging. A lead configuration with a ring electrode that extends around substantially the entire periphery of the lead body, may reduce heating during MR imaging. In the MR environment, the tip electrode usually generates the most heat. Also, heating generally monotonically increases as a function of the inverse of total electrode surface area. Therefore, an increase in the size of the most distal electrode may decrease heating. A lead with a ring electrode proximate to its distal tip, such as electrode 40 on lead 2 (FIG. 3), may provide advantages during MR imaging compared to a lead with only a segmented row of electrodes proximate to its distal tip. Increasing the length, e.g., in the direction of longitudinal axis 51, of the most distal electrode may also decrease MR heating.

In embodiments in which pseudo-monopolar stimulation is used, increasing the size, e.g., length or surface area, of the electrode(s) located at the most proximally located axial position may more accurately mimic a monopolar stimulation configuration that uses the casing of stimulation controller 8 (FIG. 1) as an anode. In some embodiments, the surface area of the proximal electrode may be at least approximately two times as large as the more distal electrodes on the lead. In other embodiments, the surface area of the proximal electrode may be at least three times greater than that of one or more of the other, more distal, electrodes.

Further, increased length for electrodes may be desired for safety reasons relating to the surface area of electrodes and charge density. However, stimulating a larger area may produce more undesirable side effects than selectively stimulating a smaller target area. Accordingly, ring electrodes and/or electrodes within segmented rows may have lengths of at least approximately 1 mm, at least approximately 1.5 mm, or at least approximately 2 mm.

The minimum size of each electrode may be determined based on specified charge density limits. Selecting an appropriate size for segmented electrodes may be particularly important, since these electrodes typically have a smaller surface area than ring electrodes that extend substantially around the entire periphery of a lead. A single electrode with ninety degrees of arc and a length of two millimeters, for example, may be able to safely support the maximum parameters of at least some stimulation treatments for Parkinson's disease. The size of the segmented and ring electrodes may be altered to comply with safety standards and changing treatment practices.

Using leads with segmented electrodes may allow stimulation to be more targeted to a specific area of interest. As a result of increased localization, lower stimulation settings may provide sufficient treatment. Alternatively, increased localization may reduce the side effects of stimulation treatment. If side effects are reduced, it may be desirable to increase stimulation parameters. Additionally, stimulation therapy for dystonia or other diseases may use even higher stimulation parameters than stimulation treatment for Parkinson's disease. As a further matter, increasing the surface area (e.g., increasing the arc and/or length) of the electrode(s) located at the most proximally located axial position may be desirable in embodiments in which pseudo-monopolar stimulation is used in order to more accurately mimic a monopolar stimulation configuration that uses the casing of stimulation controller 8 (FIG. 1) as an anode.

In some embodiments at least three electrodes will be used in each segmented row of electrodes. Increasing the number of electrodes per row may improve the ability to control stimulation field directionality, but may increase the risk of tissue damage due to reduced electrode surface area. A row with three relatively large arc electrodes, e.g., 90 degree arc, may exhibit approximately 70% as much directionality as a row with four smaller arc electrodes, e.g., 60 degree arc. Alternatively, two electrodes per segmented row may be used. Using two electrodes per row may be beneficial, if stimulating one side of the lead body while avoiding stimulation of the other side is desirable. However using two electrodes per row may result in reduced ability to steer the electrical field. Further, more than four electrodes per row may be used in some embodiments.

In some embodiments, each lead may have a total of eight electrodes, such as lead 2 with electrodes 40, 42A-42C, 44A-44C, and 46 illustrated in FIG. 3, and each electrode may be independently controlled to deliver electrical pulses. For DBS, a bilateral lead configuration in which one lead is implanted in each side of the brain is used more than eighty percent of the time. Currently, some commercially available stimulators, such as the Restore family of stimulators available from Medtronic, Inc. of Minneapolis, Minn., contain sixteen conductors that may be electrically connected to the electrodes of one or more leads. Using a lead with more than eight electrodes, such as a twelve electrode lead, with a bilateral implant may require either using an adapter to down select only eight conductors, or a separate neurostimulator for each lead. Since many clinicians dislike the awkwardness and bulk of an adapter, and a second stimulator would add significant cost to a bilateral implant procedure, leads with eight or fewer electrodes may be preferred.

Providing ring electrodes and segmented rows of electrodes at four axial positions, such the arrangement of ring (40 and 46) and segmented (42 and 44) electrodes on lead 2 in FIG. 3, may be desirable. During implantation, a clinician typically aims to position the lead such that a target anatomical structure or stimulation site is between inner electrode rows 38A and 38B, i.e. at the mid-length of the electrode region. However, in some cases, the implantation is not precise. Furthermore, in some cases, the physiologically appropriate site for delivery of stimulation may be different than the anatomical target chosen by the clinician.

Providing ring electrodes and segmented rows of electrodes at four axial positions allows for increased flexibility if the actual lead implant location varies from the target lead implant location, or the physiologically appropriate site for stimulation differs for the target anatomical site. After implantation, the row closest to the target stimulation site may be selected to deliver stimulation. If the lead is implanted as intended and the physiologically appropriate site corresponds with the target anatomical site, one of inner electrode rows 38A and 28B may be selected. Alternatively, if the physiologically appropriate site for stimulation is closest to distal ring electrode 40 or proximal ring electrode 46, the activation of ring electrodes 40 or 46 would be possible. In general, inner segmented rows 38A and 138B are typically used to deliver stimulation, and the ring electrodes may be only occasionally used to deliver stimulation.

Alternatively, a 3-3-1-1 electrode configuration may be preferred by physicians who prefer to implant the lead as shallow as possible. With this configuration, the clinician implanting the lead may aim to place the lead with the target stimulation site between the two most distal segmented rows of electrodes.

In an alternative embodiment, a 1-1-3-3 electrode configuration may be used. This configuration may reduce heating during MR imaging by having two relatively large electrodes that extend substantially completely around the lead as the most distal electrodes. However, the lead may need to be implanted deeper than other configurations in order to place the segmented electrodes near a target stimulation site.

Medical leads with electrodes and electrode segments may be constructed using a variety of techniques. For example, leads may be constructed as described in commonly-assigned and co-pending U.S. application Ser. Nos. 11/343,752 and 11/343,667, by Hegland and Stone, filed on Jan. 31, 2006, and entitled "METHOD OF MANUFACTURING A MEDICAL LEAD" and "A MEDICAL LEAD WITH SEGMENTED ELECTRODE," respectively, which are incorporated herein by reference in their entirety.

Various embodiments of the invention have been described. These and other embodiments are within the scope of the following claims.

The invention claimed is:

1. A medical lead comprising:
   an elongated lead body that includes a proximal portion configured for coupling the medical lead to a stimulation controller and a distal portion, wherein the lead body defines a longitudinal axis;
   a first ring electrode and a second ring electrode respectively located at first and second axial positions on the distal portion of the lead body; and
   a segmented row of electrodes located at a third axial position on the distal portion of the lead body, wherein each of the electrodes of the segmented row extends around only a portion of a periphery of the lead body.

2. The medical lead of claim 1, wherein the first axial position comprises the most distal position of the first, second, and third axial positions.

3. The medical lead of claim 2, wherein the second axial position comprises the most proximal position of the first, second, and third axial positions.

4. The medical lead of claim 1, wherein the segmented row of electrodes comprises a first row, further comprising a plurality of additional segmented rows of electrodes, each of the additional rows located at a respective axial position on the distal end of the lead body.

5. The medical lead of claim 4, wherein each of the additional rows is located between the first ring electrode and the second ring electrode.

6. The medical lead of claim 1, wherein the segmented row of electrodes comprises a first row, the medical lead further comprising a second segmented row of electrodes located at a fourth axial position.

7. The medical lead of claim 6, wherein third and fourth axial positions are between the first and second axial positions.

8. The medical lead of claim 6, wherein the third and fourth axial positions are more distal than the first and second axial positions.

9. The medical lead of claim 6, wherein the third and fourth axial positions are more proximal than the first and second axial positions.

10. The medical lead of claim 1, wherein the lead body has a substantially cylindrical cross-sectional shape.

11. The medical lead of claim 1, wherein the electrodes of the segmented row are substantially aligned on a common plane that is substantially perpendicular to the longitudinal axis defined by the elongated lead body.

12. The medical lead of claim 1, wherein the segmented row comprises at least three electrodes distributed around the periphery of the lead body.

13. The medical lead of claim 1, wherein the medical lead comprises a deep brain stimulation (DBS) lead.

14. The medical lead of claim 1, wherein the first axial position is the most proximal of the axial positions, and the first axial position is axially displaced from an adjacent one of the axial positions by greater than approximately three millimeters.

15. The medical lead of claim 1, wherein the first axial position is the most proximal of the axial positions, and a first distance between the first axial position and an adjacent one of the second and third axial positions is at least approximately two times as large as a second distance between the adjacent one of the second and third axial positions and a distal one of the second and third axial positions.

16. A medical lead comprising:
an elongated lead body that includes a proximal portion configured for coupling the medical lead to a stimulation controller device and a distal portion, wherein the lead body defines a longitudinal axis;
a first ring electrode and a second ring electrode respectively located at first and second axial positions on the distal end of the lead body;
a first segmented row of electrodes at a third axial position on the distal end of the lead body; and
a second segmented row of electrodes at a fourth axial position on the distal end of the lead body, wherein each of the electrodes of the segmented rows extends around only a portion of a periphery of the lead body.

17. The medical lead of claim 16, wherein the third and fourth axial positions are between the first and second axial positions.

18. The medical lead of claim 16, wherein the third and fourth axial positions are more distal than the first and second axial positions.

19. The medical lead of claim 16, wherein the third and fourth axial positions are more proximal than the first and second axial positions.

20. The medical lead of claim 16, wherein the lead body has a substantially cylindrical cross-sectional shape.

21. The medical lead of claim 16, wherein, for each of the segmented rows, the electrodes of the row are substantially aligned on a common plane that is substantially perpendicular to the longitudinal axis defined by the elongated lead body.

22. The medical lead of claim 16, wherein each of the first and second rows comprises three electrodes distributed around the periphery of the lead body.

23. The medical lead of claim 16, wherein the medical lead comprises a deep brain stimulation (DBS) lead.

24. The medical lead of claim 16, wherein the first axial position is the most proximal of the axial positions, and the first axial position is axially displaced from an adjacent one of the axial positions by greater than approximately three millimeters.

25. The medical lead of claim 16, wherein the first axial position is the most proximal of the axial positions, and a first distance between the first axial position and an adjacent one of the axial positions is at least approximately two times as large a second distance between another pair of adjacent axial positions.

26. A system comprising:
a medical lead, wherein the medical lead comprises:
an elongated lead body that includes a proximal portion and a distal portion,
wherein the lead body defines a longitudinal axis;
a plurality of electrodes, wherein the plurality of electrodes comprises:
a ring electrode located at a first axial position on the distal portion of the lead body; and
a segmented row of electrodes located at a second axial position on the distal portion of the lead body wherein each of the electrodes of the segmented row extends around only a portion of a periphery of the lead body; and
a stimulation controller that delivers electrical stimulation via a selected combination of the plurality of electrodes of the medical lead, wherein the proximal portion of the medical lead is configured for coupling the medical lead to the stimulation controller.

27. The system of claim 26, further comprising a second ring electrode at a third axial position.

28. The system of claim 27, wherein the first axial position comprises the most distal position of the first, second, and third axial positions.

29. The system of claim 27, wherein the segmented row of electrodes comprises a first row, the medical lead further comprising a second segmented row of electrodes located at a fourth axial position.

30. The system of claim 29, wherein third and fourth axial positions are between the first and second axial positions.

31. The system of claim 29, wherein the third and fourth axial position are more distal than the first and second axial positions.

32. The system of claim 29, wherein the third and fourth axial position are more proximal than the first and second axial positions.

33. The system of claim 28, wherein the third axial position comprises the most proximal position of the first, second, and third axial positions.

34. The system of claim 26, wherein the segmented row of electrodes comprises a first row, further comprising a plurality of additional segmented rows of electrodes, each of the additional rows located at a respective axial position on the distal end of the lead body.

35. The system of claim 34, wherein each of the additional rows is located between the first ring electrode and the second ring electrode.

36. The system of claim 26, wherein the lead body has a substantially cylindrical cross-sectional shape.

37. The system of claim 26, wherein the electrodes of the segmented row are substantially aligned on a common plane that is substantially perpendicular to the longitudinal axis defined by the elongated lead body.

38. The system of claim 26, wherein the segmented row comprises at least three electrodes distributed around the periphery of the lead body.

39. The system of claim 26, wherein the stimulation controller delivers deep brain stimulation (DBS) via the lead.

40. The system of claim 26, wherein the first axial position is the most proximal of the axial positions, and the first axial position is axially displaced from an adjacent one of the axial positions by greater than approximately three millimeters.

41. The system of claim 26, wherein the first axial position is the most proximal of the axial positions, and a first distance between the first axial position and an adjacent one of the axial positions is at least approximately two times as large as a second distance between the adjacent one of the axial positions and a distal one of the axial positions.

* * * * *